United States Patent [19]

Failla

[11] Patent Number: 4,693,248
[45] Date of Patent: Sep. 15, 1987

[54] TWO-PIECE TISSUE FASTENER WITH DEFORMABLE RETAINING RECEIVER

[75] Inventor: Stephen J. Failla, Chester, N.J.

[73] Assignee: Ethicon, Inc.

[21] Appl. No.: 759,795

[22] Filed: Jul. 29, 1985

Related U.S. Application Data

[63] Continuation-in-part of Ser. No. 506,144, Jun. 20, 1983, abandoned.

[51] Int. Cl.⁴ .............................................. A61B 17/04
[52] U.S. Cl. ........................... 128/334 C; 227/DIG. 1; 411/339
[58] Field of Search ............ 128/346, 337, 335, 334 R, 128/334 C, 330, 325, 326, 92 B; 3/1; 227/DIG. 1, 15-18, 77; 411/469, 451, 360, 501, 506, 362-364, 455-457, 339; 24/543, 518, 614, 623, 703, 297, 150 FP, 16 PB, 697, 580-581, 584, 453, 30.5 P, 537, 515, 513, 503, 94-96

[56] References Cited

U.S. PATENT DOCUMENTS

| Re. 27,391 | 6/1972 | Merser | 24/150 FP X |
|---|---|---|---|
| 306,479 | 10/1884 | Goddard | 24/95 |
| 389,660 | 9/1888 | Mandel et al. | 411/457 X |
| 579,831 | 3/1897 | Ketchum | 24/95 |
| 1,988,233 | 1/1935 | Berendt | 24/95 |
| 2,794,981 | 6/1957 | Brayton | 227/15 |
| 2,881,762 | 4/1959 | Lowrie | 128/337 |
| 2,897,561 | 8/1959 | Megibow | 24/95 |
| 2,900,696 | 8/1959 | Bacon | 24/614 X |
| 3,009,852 | 11/1961 | Gruner | 128/330 X |
| 3,166,072 | 1/1965 | Sullivan | 128/346 X |
| 3,210,820 | 10/1965 | Humiston | 24/584 X |
| 3,326,217 | 6/1967 | Kerr | 227/DIG. 1 C X |
| 3,357,296 | 12/1967 | Lefever | 128/334 C X |
| 3,494,006 | 2/1970 | Brumlik | 411/456 X |
| 3,570,497 | 3/1971 | Lemole | 128/335.5 |
| 3,577,601 | 5/1971 | Mariani et al. | 24/16 |
| 3,683,927 | 8/1972 | Noiles | 128/326 X |
| 3,744,495 | 7/1973 | Johnson | 128/330 |
| 3,802,438 | 4/1974 | Wolvek | 128/335 |
| 3,857,396 | 12/1974 | Hardwick | 128/335 |
| 3,875,648 | 4/1975 | Bone | 227/19 X |
| 3,981,051 | 9/1976 | Brumlik | 411/456 X |
| 4,006,747 | 2/1977 | Kronenthal et al. | 128/337 X |
| 4,038,725 | 8/1977 | Keefe | 24/150 FP |
| 4,060,089 | 11/1977 | Noiles | 128/337 X |
| 4,235,238 | 11/1980 | Ogiu et al. | 128/335 X |
| 4,259,959 | 4/1981 | Walker | 128/337 |
| 4,294,255 | 10/1981 | Geroc | 128/334 C |
| 4,326,531 | 4/1982 | Shimonaka | 128/326 |
| 4,400,833 | 8/1983 | Kurland | 3/1 |
| 4,402,445 | 9/1983 | Green | 128/334 R X |
| 4,454,875 | 6/1984 | Pratt et al. | 128/92 B |
| 4,487,205 | 12/1984 | Di Giovanni et al. | 128/346 X |

FOREIGN PATENT DOCUMENTS

| 1097171 | 3/1981 | Canada | 128/330 |
|---|---|---|---|
| 1385691 | 12/1964 | France | 40/300 |
| 8301190 | 4/1983 | PCT Int'l Appl. | 227/DIG. 1 |
| 82738 | 10/1919 | Switzerland | 128/330 |
| 972731 | 10/1964 | United Kingdom | 128/346 |

*Primary Examiner*—Michael H. Thaler

[57] ABSTRACT

A fastener is provided to hold together portions of mammalian tissue and includes an open loop fastening member and a receiver with two passages for receiving the legs of the fastening member. The receiver defines a plurality of deformable projections spaced peripherally around the interior surface of each passage for being deformed as one of the legs is received in the passage to thereby effect an interference fit engagement and inhibit withdrawal of the leg from the receiver.

9 Claims, 7 Drawing Figures

TWO-PIECE TISSUE FASTENER WITH DEFORMABLE RETAINING RECEIVER

This is a continuation-in-part application of co-pending patent application Ser. No. 506,144 filed June 20, 1983, now abandoned.

TECHNICAL FIELD

This invention relates, in general, to the fastening together of portions of tissue in surgical procedures.

BACKGROUND OF THE INVENTION

In various surgical procedures, fasteners in the form of staples or the like are employed for holding tissue portions together to facilitate healing of a wound or incision. For example, a locking staple, having a tongue and groove structure by which the staple is locked, is disclosed in U.S. Pat. No. 2,881,762. A metal staple especially adapted for ligating blood vessels is disclosed in U.S. Pat. No. 3,079,608. International patent application No. PCT/SU79/00049 discloses a variety of fastening devices and instruments for performing circular anastomoses on the large intestine. The aforementioned disclosures serve as examples of a wide variety of tissue fastening devices and techniques that may be employed in general and/or specific surgical situations.

One common type of fastening device for joining or holding together soft tissue portions is the generally "U"-shaped staple which is typically fabricated from a suitable metal. Such staples, although generally described as having two legs joined to define a "U"-shape when unclinched, may also be regarded as having a configuration of an "open" loop when unclinched. The legs need not necessarily be parallel but are typically adapted for penetrating the tissue portions and for receiving between them some of the tissue material.

Other examples of U-shaped or open loop staples, as well as of methods and instruments for applying such staples to tissue, are disclosed in U.S. Pat. Nos. 3,252,643, 3,482,428, 3,692,224, 3,790,057, 3,795,034, 3,889,683, 4,198,982, 4,316,468, and 4,319,576.

Other tissue fastening devices have been proposed and differ from staples per se in that these other devices may have a plurality of components and do not have to be clinched in the manner used to set a staple. One such device is disclosed in U.S. Pat. No. 4,060,089 and includes a fastener strip provided with a plurality of longitudinally spaced, parallel prongs which are adapted to penetrate two overlapped tissue portions from one side so that the distal ends of the prongs project from the other side of the tissue portions.

The fastener device further includes a retainer strip which is adapted to be placed on the other side of the tissue portions opposite the fastener strip to engage the ends of the projecting fastener strip prongs and thus secure the tissue portions tightly between the fastener strip and the retainer strip. The retainer strip defines frustoconical openings for receiving the fastener strip prongs which each include a plurality of spaced-apart, frustoconical engaging members for engaging the retainer strip at a desired position relative to the prongs. This provides for the capability of adjusting the distance between the fastener strip and the retainer strip. Such a fastening device may be fabricated from a biodegradable or absorbable material.

Yet another tissue fastening device having a plurality of components is disclosed in co-pending commonly assigned U.S. patent application Ser. No. 359,443 filed Mar. 18, 1982, abandoned. The fasteners disclosed in that application are made from various polymeric materials and the legs of the U-shaped staple portion of the fastener have a pointed taper to improve the penetration of the staple into tissue.

Although many of the above-discussed types of tissue fastening devices and techniques are satisfactory in various applications, there is a need to provide an improved fastening device, especially one completely fabricated from absorbable materials.

Also, it would be desirable to provide an improved fastening device fabricated from absorbable materials that can provide primary approximation of the tissue edges to insure that the tissue edges are in continuous contact. Further, such an improved fastener should provide a desired amount of hemostatic compression to minimize bleeding, but allow some collateral blood circulation to the wound or incision edges of the tissue to promote healing. In addition, such an improved fastener should have the capability to accommodate varying tissue thicknesses and should leave as little tissue cuff or margin as possible in effecting the joining of the tissue.

It is also desirable that the fastener cause as little trauma to tissue as possible. Hence when using a "U"-shaped fastener the legs of the "U" should be smooth, free of projection, so that the leg will readily penetrate tissue without tearing or causing undo trauma of the tissue.

Because humans are of different sizes and configurations and because tissue in the human body is of varying thickness it is desirable that polymeric fasteners be locked or set in place at any desired thickness and not at some predetermined thickness.

Further, it would be beneficial if such an improved fastener had a configuration that would enable the fastener to be fabricated with as small a size as possible to minimize the amount of implantable material. Also, another desirable feature of such an improved fastener would be a fastener configuration that minimizes the possible sites of formation of pockets of infection in the tissue.

Further, such an improved fastener would desirably provide the surgeon with tactile feedback and compensating control during the application of the fastener.

Finally, such an improved fastener should have the capability for maintaining the tissue portions in approximation and compression for a minimum of 21 days in vivo.

It would also be advantageous to provide such a fastener with a design that would facilitate its application to the tissue portions with a simple yet effective method. It would also be desirable if the improved fastener could readily accommodate application by means of an appropriately designed instrument.

SUMMARY OF THE INVENTION

An improved polymeric fastener is provided to hold together portions of mammalian tissue, such as are defined by a wound or incision, to facilitate healing of the wound or incision. The fastener includes an open loop fastening member comprising a pair of legs with distal ends adapted to penetrate the tissue portions and a link connecting the legs that is adapted to be disposed adjacent one of the tissue portions. The legs of the fastening member are smooth and free of projections.

The fastener also includes a rigid, non-deformable receiver adapted to be disposed against the other of the tissue portions opposite the fastening member. The receiver defines one passage therein for receiving one of the fastening member legs after the legs have been inserted through the tissue portions and defines another passage therein for receiving the other of the fastening member legs after the legs have been inserted through the tissue portions. The rigid receiver further defines a plurality of deformable projections spaced peripherally around the interior surface of each passage for being deformed without deforming the receiver as a leg is received in each passage to thereby effect an interference fit engagement and inhibit withdrawal of the legs from the receiver. By "interference fit" it is meant the frictional contact between the surface of the leg of the fastening member and the deformable projections. This allows the fastening member and the receiver to be locked together at any desired location along the leg and allows the fastener to accommodate tissue having a wide variety of thickness.

Numerous other features of various embodiments of a novel tissue fastener will be apparent from the following detailed description and accompanying drawings.

BRIEF DESCRIPTION OF THE DRAWINGS

In the accompanying drawings forming part of the specification, and in which like numerals are employed to designate like parts throughout the same.

DESCRIPTION OF THE PREFERRED EMBODIMENTS

Figure 1:
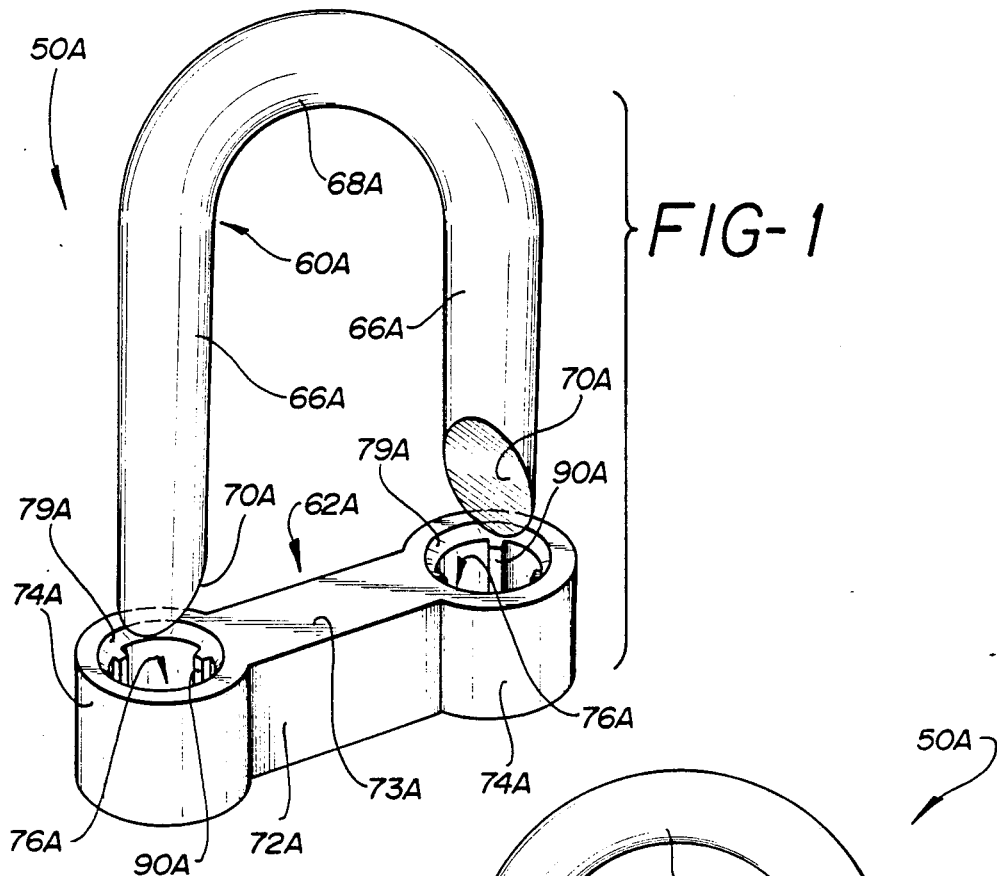
FIG. 1 is a perspective view of the fastener of the present invention which includes a fastening member and receiver.

This invention may be used in many different forms. The specification and accompanying drawings disclose only a few specific forms as an example of the use of the invention. The precise shapes and sizes of the components herein described are not essential to the invention unless otherwise indicated. The invention is not intended to be limited to the embodiments illustrated, and the scope of the invention is pointed out in the appended claims.

FIRST EMBODIMENT OF THE FASTENER

A first embodiment of the fastener is illustrated in FIGS. 1–4 and is designated generally therein by reference numeral 50A.

Figure 3:
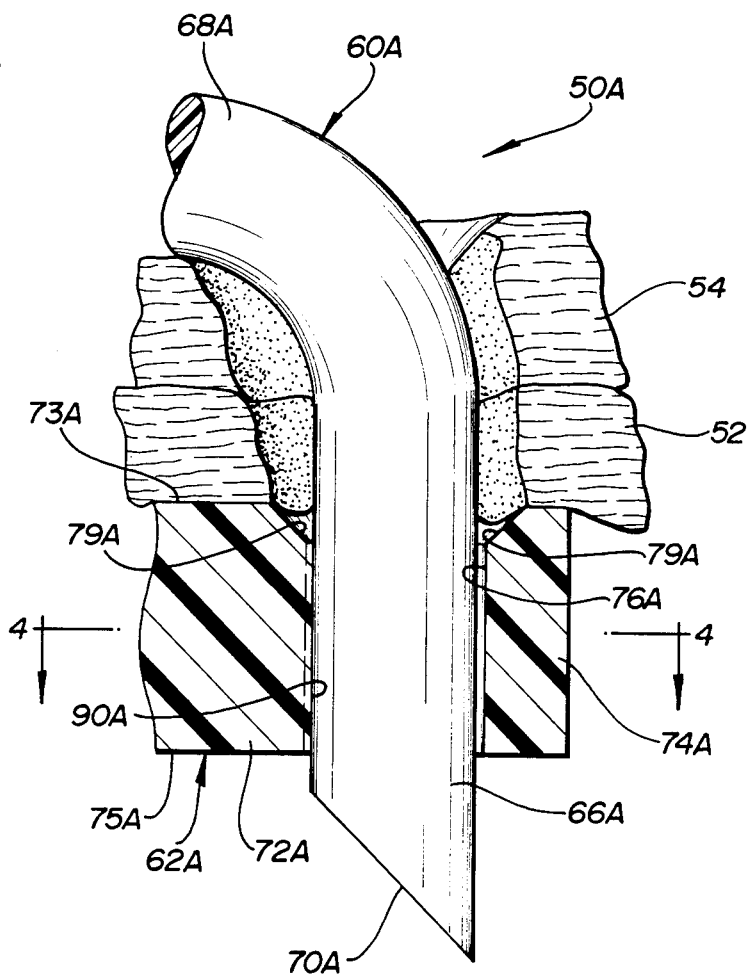
FIG. 3 is a greatly enlarged, fragmentary view similar to FIG. 2 but showing the fastening member and receiver fully engaged.

The fastener 50A is illustrated in FIG. 3 in the fully assembled, "set" configuration wherein it is shown holding together two portions 52 and 54 of mammalian tissue, such as are defined by a wound or incision, to facilitate healing of the wound or incision. Typically, a plurality of such fasteners 50A would be used to close a wound or incision. However, with just a small wound or incision, one fastener 50A may be sufficient. The fastener 50A includes two components, a generally U-shaped or open loop fastening member 60A and a receiver 62A, which are initially separated as illustrated in FIG. 1 and which are adapted to cooperate to compress or hold between them the tissue portions.

Figure 2:
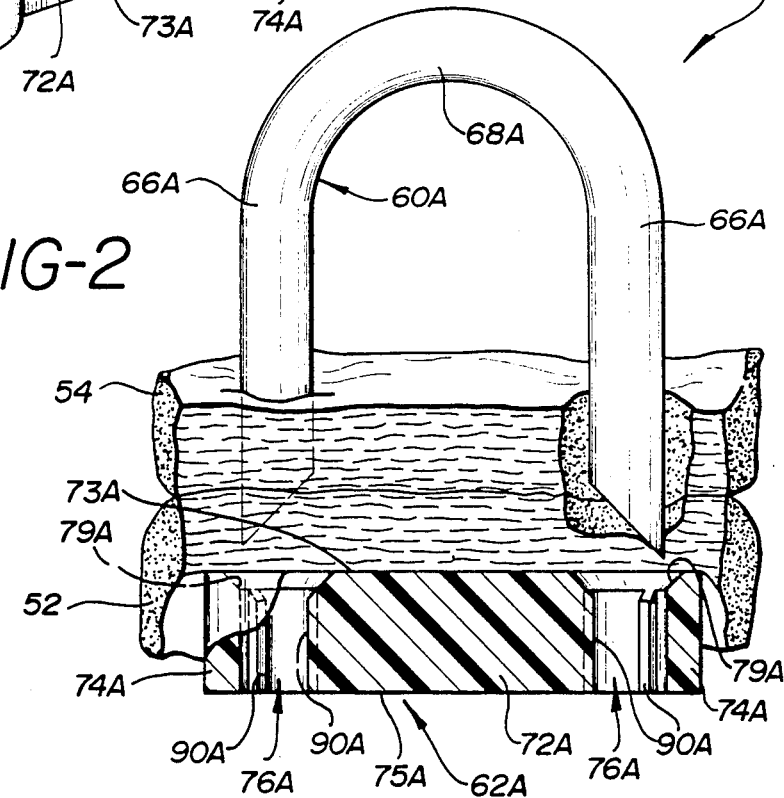
FIG. 2 is a fragmentary, partial cross-sectional view of two portions of mammalian tissue defined by an incision or wound with some of the tissue cut away to better show interior detail and illustrating (1) the fastening member of FIG. 1 being inserted by suitable means (not illustrated) into the two portions of the tissue and (2) the receiver of FIG. 1 being held against the tissue portions by suitable means (not illustrated)

As is best illustrated in FIGS. 1 and 2, the fastening member 60A includes (1) a pair of legs 66A adapted to penetrate the tissue portions and (2) a joining portion, link, or clamping member 68A which connects, and is connected to, the legs 66A. The link 68A is adapted to be disposed adjacent (i.e., lie over and/or substantially against) one of the tissue portions (e.g., tissue portion 54 in FIG. 3) whereas the legs 66A are adapted to penetrate the tissue portions.

The legs 66A of the fastening member are generally parallel to each other. Preferable, each leg 66A has a solid, generally cylindrical configuration terminating in a distal end with a pointed end generally formed by an elliptical face 70A defined by an oblique section so as to facilitate or aid in the penetration of the tissue portions.

In the embodiment illustrated in FIGS. 1 and 2, the link or clamping member 68A is arcuate (e.g., having an arch shape) and merges with the legs 66A. The link 68A has a generally cylindrical transverse cross-section. However, if desired, the link may be straight or generally perpendicular to the legs 66A and may have some other suitable cross-sectional shape.

As best illustrated in FIGS. 1 and 2, the receiver 62A includes a central portion or member 72A joining a pair of leg receiving members 74A. The receiver 62A has a first side 73A (FIG. 1) adapted to be disposed against a tissue portion (tissue portion 52 shown in FIGS. 2 and 3). The receiver 62A also has a second side 75A (FIG. 2) parallel to, and facing generally away from, the first side 73A. The vertical surfaces of the receiving members 74A and of the central portion 72A define a continuous exterior peripheral surface extending between the first side 73A and the second side 75A.

Each receiving member 74A of the receiver 62A defines a passage 76A, which may be a cylindrical bore as illustrated, for receiving one of the fastening member legs 66A after the legs have been inserted through the tissue portions. Each passage 76A has a configuration adapted to accommodate one of the fastening member legs 66A. Preferably, each passage 76A has a transverse cross-sectional configuration generally similar to, and larger than, the transverse cross-sectional configuration of the associated fastening member leg 66A.

The receiver 62A further defines a plurality of deformable projections 90A which are spaced peripherally around the interior surface of the passage 76A for being deformed as one of the legs is received in the passage to thereby effect an interference fit engagement and inhibit withdrawal of the leg from the receiver 62A. In the first embodiment illustrated in FIGS. 1–4, each projection 90A is rib-like and has a generally rectangular transverse cross-section (before deformation resulting from insertion of the fastener leg 66A). Preferably, the projections 90A are uniformly spaced around the interior of the passage 76A. In the first embodiment illustrated in FIGS. 1–4, the projections 90A are spaced at 120° intervals around the passage 76A. The projections 90A extend along at least a portion of the length of the passage 76A. The particular shape of the illustrated passage 76A can thus be regarded as being defined, in part, by a plurality of partially cylindrical surfaces oriented about a longitudinal axis normal to the receiver first and second sides 73A and 75A, respectively, with each projection 90A being located between two of the partially cylindrical surfaces.

As best illustrated in FIGS. 1-3, the receiver 62A defines a frustoconical surface 79A around the passage 76A at the receiver first side 73A. As a result, the elongate rib projections 90A terminate at one end inwardly of the receiver side surface 73A and at the opposite end at side surface 75A.

The fastening member 60A and receiver 62A may be formed from suitable materials, such as thermoplastic polymer materials that are absorbable by mammalian tissue. For example, the fastening member and receiver may be molded from absorbable polymers or copolymers of poly-dioxanone, lactide, glycolide and the like. The fastener may also be molded from a combination of both such materials. The receiver 62A, or at least the projections 90A in the receiver 62A, are fabricated from a material that is deformable (relative to the material of the fastening member legs 66A) under the application of the forces imposed by insertion of the fastening member legs.

The fastener 50A is used to join the tissue portions 52 and 54 (FIGS. 2 and 3) in a novel manner. Specifically, the tissue portions 52 and 54 are first approximated in surface-to-surface relationship as best illustrated in FIG. 2. Then the fastening member 60A is positioned on one side of the tissue portions with the legs 66A oriented at an appropriate angle to penetrate the tissue portions. The receiver 62A is held on the other side of the tissue portions opposite the fastening member 60A and generally in alignment with the fastening member legs 66A. Specifically, the passages 76A are aligned with the fastening member legs 66A. Next, relative movement between the fastening member 60A and the receiver 62A is effected to urge the fastening member and the receiver closer together to cause the fastening member legs 66A to penetrate the tissue portions 52 and 54 and to locate at least portions of the fastening member legs 66A within the receiver 62A. The relative movement between the fastening member 60A and the receiver 62A is terminated when the fastening member link 68A is at a desired distance from the receiver 62A to secure the tissue portions together. Preferably, this movement is terminated after the tissue portions have been compressed together a desired amount.

Figure 4:
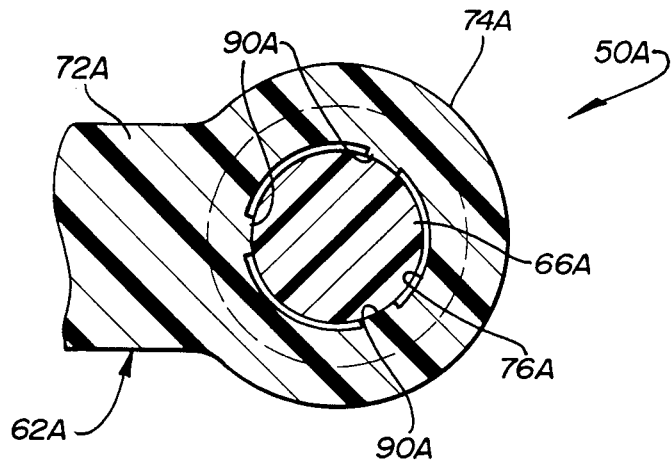
FIG. 4 is a fragmentary, cross-sectional view taken generally along the plane 4—4 in FIG. 3.

As the fastening member legs 66A are pushed though the receiving members 74A, each leg engages the projections 90A and causes portions of the projections 90A to be deformed inwardly, laterally, and downwardly to facilitate passage of the leg therepast. In FIGS. 3 and 4, the leg 66A is shown in the final position with the projections 90A deformed to thereby effect an interference fit engagement and inhibit withdrawal of the leg from the receiver. In certain embodiments of the present invention, the legs may also deform to a slight degree.

When the tissue portions 54 and 52 have been compressed the desired amount, the applied forces effecting the relative movement between the fastening member 60A and the receiver 62A are removed. Although oppositely directed forces are exerted by the compressed tissue portions 52 and 54 on the fastening member 60A and receiver 62A, the interference fit engagement withstands these forces so that the fastener holds the tissue portions together.

The distal ends of the fastening member legs 66A may or may not protrude from the receiver 62A opposite the side of the receiver that is contacting one of the tissue portions. If desired, the protruding ends of the legs 66A may be severed flush with the bottom of the receiver 62A by a suitable means. Preferably, during the step of severing the protruding portions of the fastening member legs 66A, the protruding portions of the fastening member legs are surrounded with a suitable container for catching the leg protruding portions after they are severed so as to prevent the severed portions of the legs from falling into the surrounding tissue or body cavity.

The above-described method for applying the fastener 50A to the tissue portions 52 and 54 may be effected with a suitable instrument specifically designed for holding the fastening member 60A and receiver 62A and for driving the fastening member 60A through the tissue portions and into engagement with the receiver 62A. Such an instrument (not illustrated) may include a pair of pivotally mounted jaws with one of the jaws adapted for holding the receiver 62A on one side of the tissue portions and with the other of the jaws adapted for holding the fastening member 60A on the other side of the tissue portions. A suitable driving member may be provided as part of the instrument for driving the fastening member 60A out of its holding jaw, into the tissue portions, and finally into engagement with the receiver 62A.

The instrument may include a suitable mechanism for severing the protruding portions of the fastening member legs 66A after the fastening member 60A and receiver 62A have been locked together with the tissue portions under the desired amount of compression. It is to be realized that such an instrument might be preferably provided with means for applying a plurality of such fasteners simultaneously. It has been found that the above-described structure, wherein each leg 66A of the fastening member 60A is smaller than the receiver passage 76A, avoids potential problems in applying the fastener to the tissue portions. For example, consider a different design wherein the projections 90A were eliminated and each fastening member leg 66A was made a small amount larger than passage 76A so as to provide an interference fit. In such a case, the manufacturing tolerances would have to be very carefully controlled. If the passages 76A were a bit too large (or conversely, if the legs 66A were a bit too small), then the fastening member 60A and receiver 62A would fit together loosely without engagement. On the other hand, if the passages 76A were too small relative to the legs 66A, then initial insertion of the legs 66A into the passages 76A might be entirely precluded. The situation is exacerbated where the fastener is fabricated from thermoplastic material and is relatively small to facilitate use as a fastener within mammalian tissue. The control of manufacturing techniques to provide the proper size passage 76A and proper size leg 66A could be difficult and expensive if an interference fit were desired between the entire peripheral surface of the leg and the entire peripheral surface of the passage 76A.

The structure of the present invention overcomes this problem and does not require the maintenance of extremely small tolerances relative to the passages 76A and the legs 66A. Rather, by incorporating the deformable projections in the receiver 62A on the interior of each passage 76A, some variation in the size of the passage 76A and/or in the size of the leg 66A is acceptable and will not prevent the maintenance of a satisfactory interference fit engagement. This is because there is a sufficient range of engagement (consisting of a major portion of the radial extension of the projection 90A) wherein withdrawal of the fastener member leg 66A will be effectively inhibited.

Owing to the deformable nature of the projections 90A (relative to the fastening member leg 66A), an adquate engagement is effected if just a small portion of each projection 90A is deformed as well as if a much larger portion of each projection 90A is deformed.

ADDITIONAL EMBODIMENTS OF THE FASTENER

Figure 5:
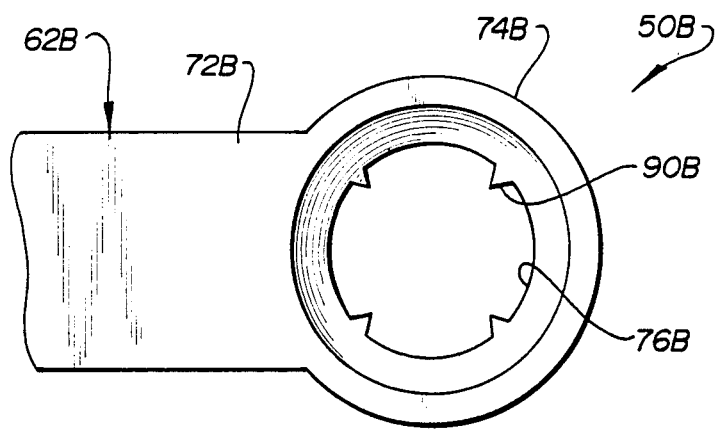
FIGS. 5, 6, and 7 are each a fragmentary, plan views of second, third, and fourth embodiments, respectively, of a receiver of the fastener of the present invention.
Figure 6:
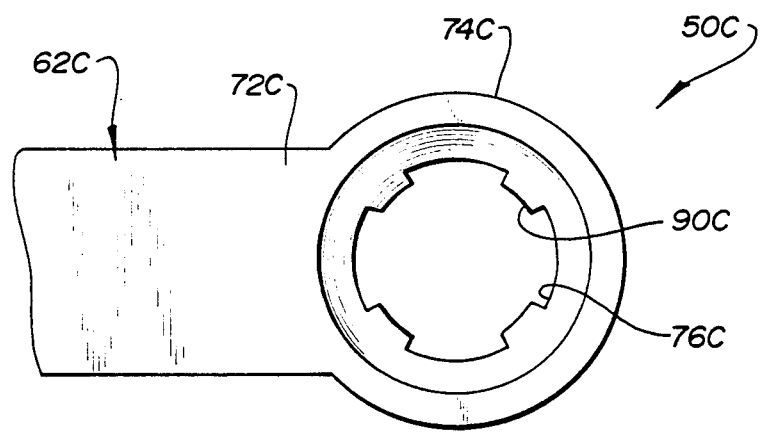
Figure 7:
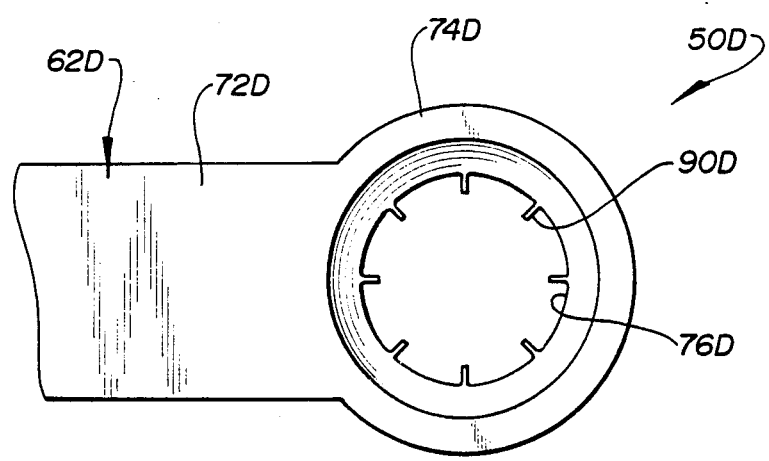

The second, third, and fourth embodiments of the fastener are illustrated in FIGS. 5, 6, and 7, respectively, and are designated generally therein by reference numerals 50B, 50C, and 50D, respectively. The fasteners 50B, 50C, and 50D, respectively are each similar to the first embodiment of the fastener 50A described above with reference to FIGS. 1-4. The elements of the fasteners 50B, 50C, and 50D that are identical or functionally analogous to those of the first embodiment of the fastener 50A are designated by reference numerals identical to those used for the first embodiment with the exception that the second, third, and fourth embodiment reference numerals are followed by the upper case letters B, C, and D, respectively, whereas the first embodiment reference numerals are followed by the upper case letter A.

The fasteners 50B, 50C, and 50D each include a receiver 62B, 62C, and 62D, respectively, and a fastening member (not illustrated). The fastening member is identical to the fastening member 60A of the first embodiment of the fastener 50A described above with reference to FIGS. 1-4.

The receivers 62B, 62C, and 62D are each similar to the receiver 62A of the first embodiment of the fastener 50A described above with reference to FIGS. 1-4. Each receiver 62B, 62C, and 62D includes a central member 72B, 72C, and 72D, respectively, joining a pair of leg receiving members 74B, 74C, and 74D, respectively. Each receiving member 74B, 74C, and 74D further defines a passage or bore 76B, 76C, and 76D, respectively.

The differences between the four embodiments of the receivers 62A, 62B, 62C and 62D reside in the configuration of the deformable projections. Specifically, in the second embodiment of the receiver 62B, the projections 90B, which are located on the periphery of the interior surface of the passage 76B, each have a generally triangular transverse cross section as illustrated in FIG. 5.

In the third embodiment illustrated in FIG. 6, the projections 90C have a generally trapezoidal cross section.

The fourth embodiment illustrated in FIG. 7 includes projections 90D which comprise a plurality of thin member. The thin members 90D in the fourth embodiment may be formed as mold flash if the receiver is molded from a suitable thermoplastic material.

In the first embodiment of the fastener 50A, three projections 90A are provided in each passage 76A. In the second and third embodiments of the fastener 50B and 50C, respectively, four projections 90B and 90C, respectively, are provided in each passage. However, more or less projections may be employed depending upon the relative dimensions and proportions of the particular designs. In the fourth embodiment illustrated in FIG. 7, a greater number of projections 90D are employed so as to provide sufficient interference in view of the relatively small amount of material that forms each individual projection 90D.

Although the first through the fourth embodiments of the fastener described above employ four different shapes of the projections 90A-90D, it is to be realized that other shapes and configurations may be used. Firther, the spacing between the projections in the passage may be different and, indeed, need not necessarily be uniform.

It is also to be realized that the fastening member legs need not necessarily have the circular cross section illustrated and that the receiver passage need not necessarily be generally circular in cross section. Other shapes, such as various polygon shapes, may be used for both the fastening member legs and the receiver passages. Further, the shapes of the receiver passages need not necessarily be complementary or similar to the shapes of the fastening member legs. It is sufficient that the shape and size of each passage relative to the shape and size of the fastening member leg be such that some manufacturing variance in the shape and size can be tolerated without deteriously affecting (1) proper reception of the leg within the passage and (2) deformation of the projections as necessary to effect the interference fit engagement.

ALTERNATIVE DESIGN FEATURES

In the figures, the two legs of the fastening member are connected by a portion of the fastening member (e.g., the link or clamping member) which is illustrated as being generally arched or U-shaped. In those situations where increased initial tissue compression is desired, a modified receiver structure may be provided to cooperate with the arcuate fastening member. Specifically, the receiver need not have a flat upper surface as illustrated. Rather, the upper surface of the receiver may be arcuate (e.g., convex) so as to generally match or correspond with the arcuate shape of the fastening member. This can result in an increased compression of the two tissue portions between the receiver and fastening member.

If desired, however, the cooperating tissue engaging surfaces of the receiver and fastening member may be flat. That is, the receiver could be provided with the flat top configuration as illustrated in FIGS. 1-3 and the portion of the fastening member connecting the legs could be a straight member extending in a perpendicular orientation between the two legs.

From the foregoing, it will be observed that numerous variations and modifications may be effected without departing from the true spirt and scope of the novel concept of the invention. It is to be understood that no limitation with respect to the specific articles, instruments, and methods illustrated herein is intended or should be inferred. It is, of course, intended to cover by the appended claims all such modifications as fall within the scope of the claims.

What is claimed is:

1. A polymeric fastener adapted to hold together two portions of mammalian tissue, such as are defined by a wound or incision, to facilitate healing of the wound or incision, said fastener comprising:
   an open loop fastening member comprising a pair of legs with distal ends adapted to penetrate said tissue portions and a link connecting said legs that is adapted to be disposed adjacent one of said tissue portions, said legs being smooth and free of projections; and a receiver adapted to be disposed against the other of said tissue portions opposite said fastening member, said receiver defining one passage therein for receiving one of said fastening member legs after said legs have been inserted through said tissue portions and defining another passage therein for receiving the other of said fastening member legs after said legs have been inserted through said tissue portions, said receiver further defining a plurality of deformable projections spaced peripherally around the interior surface of each said passage for being deformed as one of said legs is received in said passage to thereby effect an interference fit engagement between the exterior surface of the fastening member legs and the deformable projections and inhibit withdrawal of said leg from said receiver, said receiver being rigid and non-deformable except for said projections.

2. The fastener in accordance with claim 1 in which said fastening member is a generally U-shaped member, in which said leg has a generally solid cylindrical shape, and in which the distal end of each leg opposite said link has a pointed end so as to aid in tissue penetration.

3. The fastener in accordance with claim 1 in which said legs are generally paralled to each other and in which said link is arcuate and merges with said legs.

4. The fastener in accordance with claim 1 in which said fastening member is molded from an absorbable thermoplastic polymer and in which said receiver is molded from an absorbable thermoplastic polymer.

5. The fastener in accordance with claim 1 in which said receiver has (1) a first side adapted to be disposed against the other of said tissue portions, (2) a second side parallel to and facing generally away from said first side, and (3) an exterior peripheral surface extending between said first and second sides;

in which each said receiver passage is defined in part by a plurality of partially cylindrical surfaces oriented about a longitudinal axis normal to said receiver first and second sides; and in which said projections extend along at least a portion of the length of each said passage parallel to said longitudinal axis with each projection being located between two of said partially cylindrical surfaces.

6. The fastener in accordance with claim 5 in which said receiver defines a frustoconical surface around each passage at said first side of said receiver.

7. The fastener in accordance with claim 1 in which each said projection has a generally triangular transverse cross section.

8. The fastener in accordance with claim 1 in which each said projection has a generally rectangular transverse cross section.

9. The fastener in accordance with claim 1 in which said projections are uniformly spaced around the interior of each said passage.

* * * * *